United States Patent [19]

Fisk

[11] Patent Number: 5,239,716
[45] Date of Patent: Aug. 31, 1993

[54] SURGICAL SPINAL POSITIONING FRAME

[76] Inventor: Albert W. Fisk, 1741 Carl Dr., Rescue, Calif. 95672

[21] Appl. No.: 862,781

[22] Filed: Apr. 3, 1992

[51] Int. Cl.[5] ..................... A61G 12/00; A61G 13/10
[52] U.S. Cl. ......................................... 5/630; 5/601; 5/621; 5/632; 606/242
[58] Field of Search ............... 5/630, 621, 632, 601, 5/648; 606/240, 242; 602/39; 378/208, 209

[56] References Cited

U.S. PATENT DOCUMENTS

| | | | |
|---|---|---|---|
| 1,814,482 | 7/1931 | Miller | 5/608 |
| 2,152,734 | 4/1939 | Ford | 5/630 |
| 2,764,150 | 9/1956 | Ettinger et al. | 5/630 |
| 3,197,198 | 7/1965 | Collis | 5/601 |
| 4,398,707 | 8/1983 | Cloward | 5/621 |
| 4,527,787 | 7/1985 | Collis, Jr. | 5/601 |
| 4,712,781 | 12/1987 | Watanabe | 5/601 |
| 4,923,187 | 5/1990 | Mombrine | 5/648 |

OTHER PUBLICATIONS

Magnetic Info (Weinmann/Magnetic)–A Technical Brochure from "Magnetic Corporation" 3 Union Drive, Olney, Illinois 62450.

*Primary Examiner*—Alexander Grosz
*Attorney, Agent, or Firm*—Jerry T. Kearns

[57] ABSTRACT

A spinal positioning frame mounted atop an operating table for lateral, longitudinal and pivotal adjustment allows optimal patient positioning. A yoke mounted in a rectangular frame for reciprocal sliding movement is driven by a pneumatically controlled electric linear actuator which may be driven in an emergency by blowing into pneumatic control lines. A pair of spaced parallel flexible steel flex strips connect juxtaposed anterior and posterior fulcrum plates pivotally mounted adjacent opposite ends of the frame. A pair of patient support pads are adjustably secured by cooperating hook and loop pile fasteners to respective pad mounting plates. Slots in the pad mounting plates receive cam lock fasteners which adjustably secure the pad mounting plates to the flex strips. The actuator causes the flex strips and pads to bow convexly upwardly, while a meter indicates the degree of flex, allowing precise regulation of spinal curvature to afford maximum lumbar access. An X-ray transparent bridge pivotally secured beneath the fulcrum plates provides support for a patient's abdomen and allows insertion of an X-ray cassette beneath the bridge for precise determination and documentation of surgical coordinates and results without removing the patient from the spinal positioning frame.

20 Claims, 6 Drawing Sheets

SURGICAL SPINAL POSITIONING FRAME

BACKGROUND OF THE INVENTION

1. Field of the Invention

The present invention relates to a surgical spinal positioning frame for use in positioning, supporting and securing a patient in a desired position for a surgical procedure. A lumbar laminectomy surgical procedure, for example, is both complex and delicate. Complications such as excessive bleeding from epidural veins, injury to retroperitoneal blood vessels or tearing of spinal nerves is always possible. Prior to the development of the surgical spinal positioning frame of the present invention, patients being prepared for such spinal surgical procedures have been placed face down, with a major portion of the patient's weight supported by the abdomen. Resultant abdominal pressure has caused excessive loss of blood and excessive blood at the operation site, obscuring the surgeon's field of vision. Blood loss during a spinal operation is a function of the degree of interspinal venous engorgement, or whether the blood vessels are full and under pressure or have been allowed to drain. If adequate room is provided to accommodate the abdomen of the patient without exerting excessive pressure, then draining naturally occurs. Accordingly, it is an object of the present invention to provide a device for correctly positioning, supporting and securing a patient for a spinal surgical procedure, without exerting excessive pressure on the patient's abdomen.

It is typically desirable to support a patient prior to a spinal surgical procedure in a manner such that the spine is convexly curved. The exact curvature desired depends on the location and type of procedure to be performed. Prior to the present invention, there have been no devices available which allowed a surgeon to position a patient with the correct curvature and then X-ray to locate exact coordinates before beginning surgery. Proper positioning is crucial to the identification of damaged vertebrae. Further, prior art devices have not allowed X-rays to be taken immediately after completion of surgery, to check and document the quality of the procedure, until after the patient has been lifted and moved by operating room personnel to a gurney. Accordingly, it is an object of the present invention to provide a safe and efficient means to precisely position, support and secure a patient during spinal surgery which is X-ray compatible to facilitate exact location of surgical coordinates and to check and document results of a surgical procedure without moving the patient.

2. Description of the Prior Art

U.S. Pat. No. 2,764,150 which issued on Sep. 25, 1956 to J. J. Ettinger et al., the entire disclosure of which is hereby incorporated herein by reference, discloses a surgical spinal positioning frame which has been employed in surgical spinal procedures for many years. The Ettinger frame has been found to suffer from several drawbacks. First of all, the device is not X-ray compatible. Accordingly, X-rays can not be used to locate surgical coordinates or to check and document the results of a surgical procedure, without first moving the patient from the spinal frame. Second, the device is manually operated by a hand crank, and is thus rather slow, difficult and cumbersome to manipulate. Third, the particular mechanical mechanism employed by the Ettinger frame has proved rather unreliable. In addition to requiring frequent and expensive repairs, the device has frequently failed in an elevated position during surgical procedures, forcing operating room personnel to manually lift patients from the elevated frame.

U.S. Pat. No. 2,152,734, which issued on Apr. 4, 1939 to C. H. Ford, the entire disclosure of which is hereby incorporated herein by reference, discloses a similar frame for supporting patients during spinal surgical procedures.

U.S. Pat. No. 2,152,734, which issued on Jul. 14, 1931 to W. J. Miller, the entire disclosure of which is hereby incorporated herein by reference, discloses an operating table including a ball and socket pivot mechanism for enabling patients to be positioned in selective angularly adjusted positions for various surgical procedures.

SUMMARY OF THE INVENTION

The present invention provides an improved surgical spinal positioning frame adapted to sit atop a general surgical table which allows a patient to be easily lifted to the surgeon's optimum working height. The spinal positioning frame allows the surgeon to selectively regulate the curvature of the spine allowing maximum access to the lumbar area. The spinal positioning frame adjusts to the physique of the patient, accommodating the abdominal region, and supporting the patient on the iliac crests (hips) and by the chest. The avoidance of abdominal pressure reduces venous back pressure, damage to the retroperitoneal major blood vessels, minimizes blood loss and minimizes interference with respiration. The spinal positioning frame of the present invention is X-ray compatible, allowing the patient to be X-rayed before surgery to locate exact surgical coordinates, and after surgery to check and document surgical results.

In a preferred embodiment, the spinal positioning frame includes a yoke mounted in a rectangular frame for reciprocal sliding movement and driven by a pneumatically controlled electric linear actuator. In emergency situations, the linear actuator may be driven by blowing into pneumatic control lines. An anterior fulcrum plate is pivotally mounted to free ends of guide rods fixed for movement with the yoke. A posterior fulcrum plate is juxtaposed with the anterior fulcrum plate and is pivotally mounted at fixed pivot points on the frame. A pair of spaced parallel flexible steel flex strips connect the anterior and posterior fulcrum plates. A pair of patient support pads are adjustably secured by cooperating hook and loop pile fasteners to respective pad mounting plates. Slots in the pad mounting plates receive cam lock fasteners which adjustably secure the pad mounting plates to the flex strips. Actuation of the linear actuator causes the flex strips to bow convexly upwardly, while a meter including an indicator secured to one of the guide rods indicates the degree of flex. An X-ray transparent bridge is pivotally secured beneath the fulcrum plates to provide support for a patient's abdomen. An X-ray cassette may be inserted beneath the bridge to allow surgical coordinates to be determined precisely prior to surgery, and to allow surgical results to be checked and documented without removing the patient from the spinal positioning frame.

These and various other advantages and features of novelty which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described preferred embodiments of the invention.

DETAILED DESCRIPTION OF THE PREFERRED EMBODIMENT(S)

Figure 1:
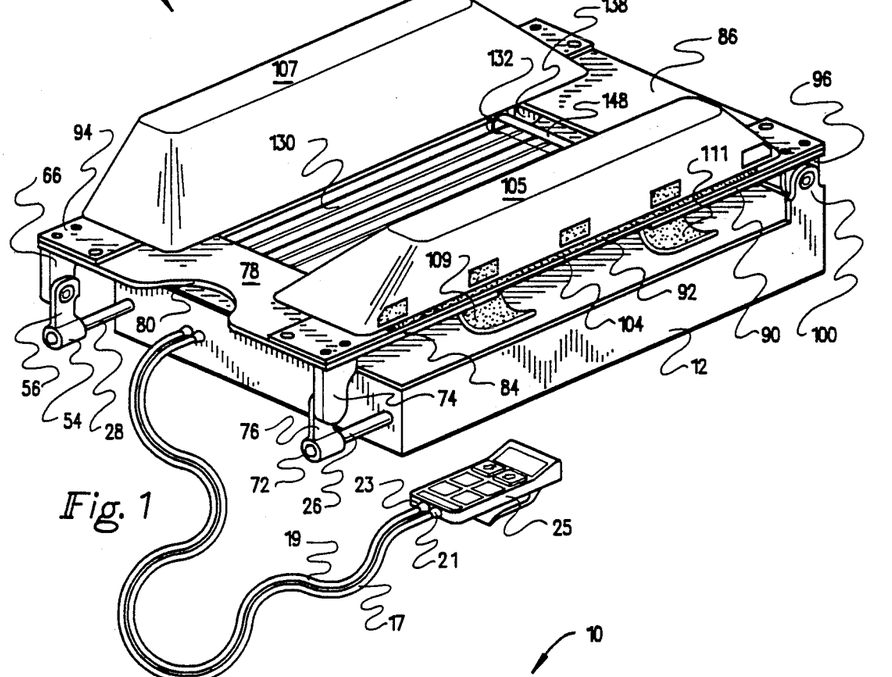
FIG. 1 is a top, front (anterior) and left side perspective view of the surgical spinal positioning frame of the present invention.
Figure 3:
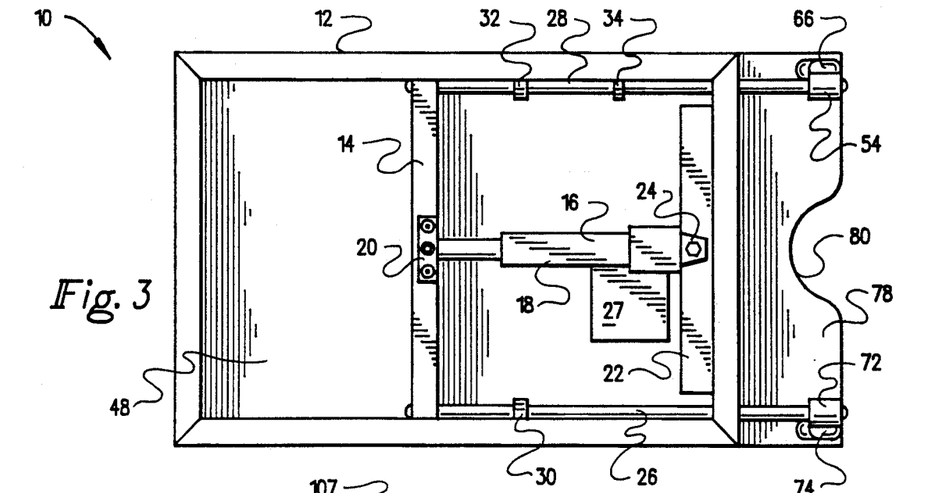
FIG. 3 is a bottom plan view of the surgical spinal positioning frame, with the bottom cover plate removed.
Figure 5:
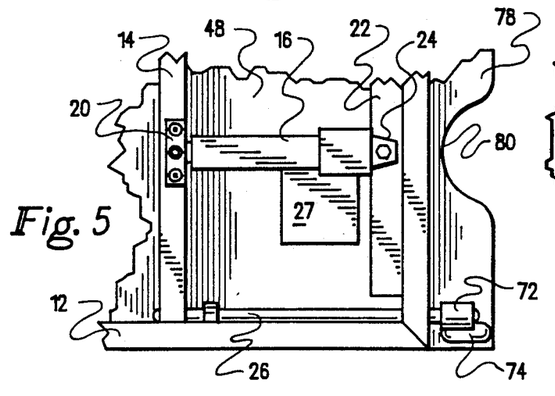
FIG. 5 is a partial bottom plan detail view of the spinal positioning frame, with the bottom cover plate removed.
Figure 7:
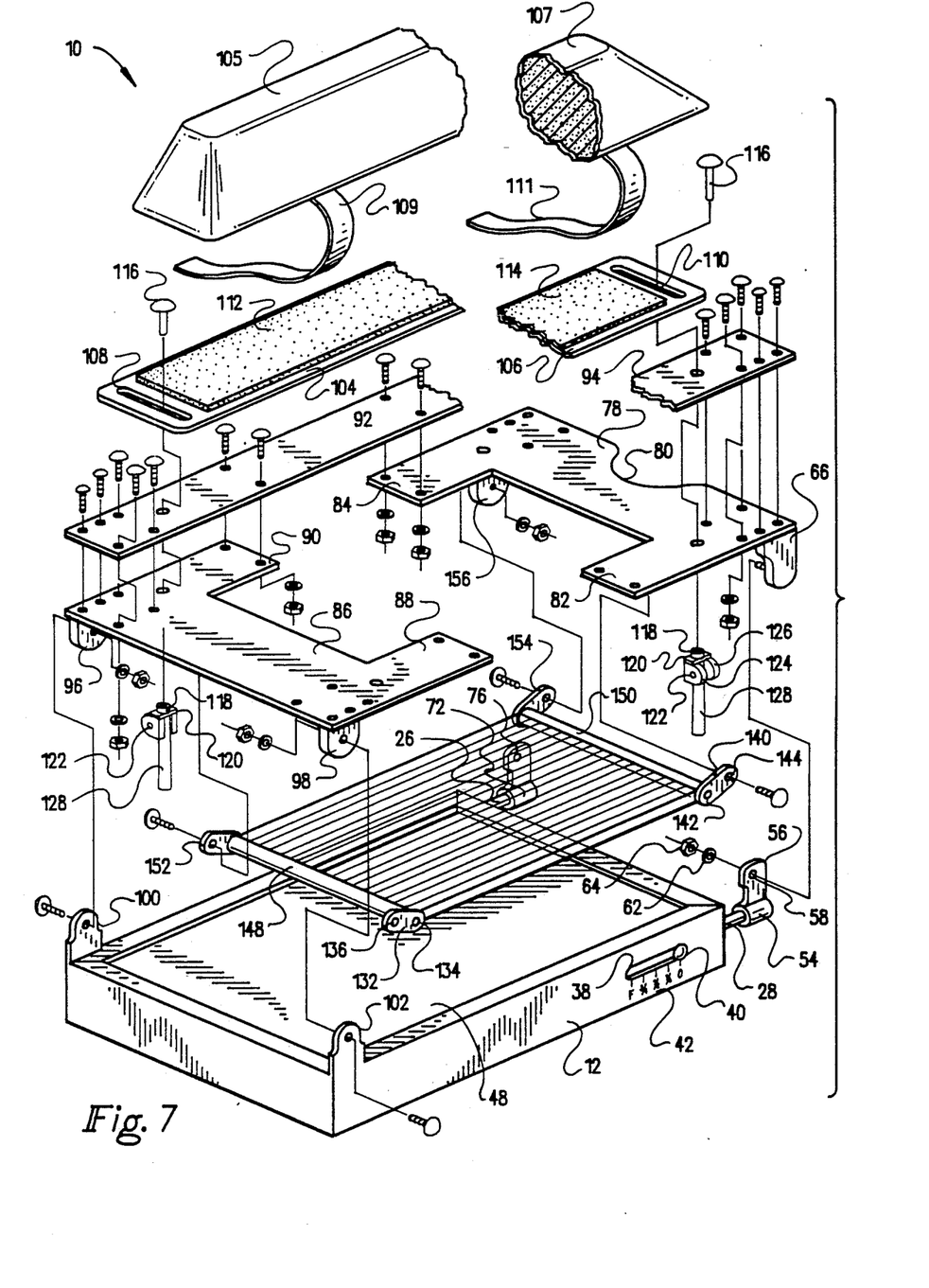
FIG. 7 is a partial exploded perspective view illustrating selected components of the spinal positioning frame.

Referring now to the drawings, wherein like reference numerals designate corresponding structure throughout the views, and referring in particular to FIGS. 1, 3 and 7, an improved surgical spinal positioning frame 10 according to a first preferred embodiment of the invention includes a rectangular frame 12 in which a transversely extending yoke 14 is mounted for reciprocal linear sliding movement. As shown in FIGS. 3 and 5, an extensible ram 18 of a pneumatically controlled electrical linear actuator 16 is secured centrally to the yoke 14 by a bracket 20. An opposite end of the linear actuator 16 is secured to a frame reinforcement rail 22 by a bracket 24. The linear actuator 16, as shown in FIGS. 3, 5, 8 and 10, includes a motor and gear reducer unit 27 operably connected to a pneumatic remote control 25 by pneumatic control lines 17 and 19. An electric motor within the gear reducer/motor portion 27 of the linear actuator 16 includes a conventional electrical power cord (not shown) for connection to a conventional AC outlet. The linear actuator 16 is preferably of the type available from Magnetic company of Liestal, Switzerland as model number SBU-11UBAK-024. This conventional electrical pneumatically controlled linear actuator may be driven in emergency situations by disconnecting the pneumatic control lines 17 and 19 from respective couplings 21 and 23 at the remote control unit 25. In the event of remote control failure, an operating individual may then selectively blow into one of the pneumatic control lines 17 or 19 to selectively extend or retract the ram 18. This feature allows a patient to be safely lowered from an elevated position, thus avoiding potential injury to the patient caused by manual lifting of the patient from the frame.

Figure 8:
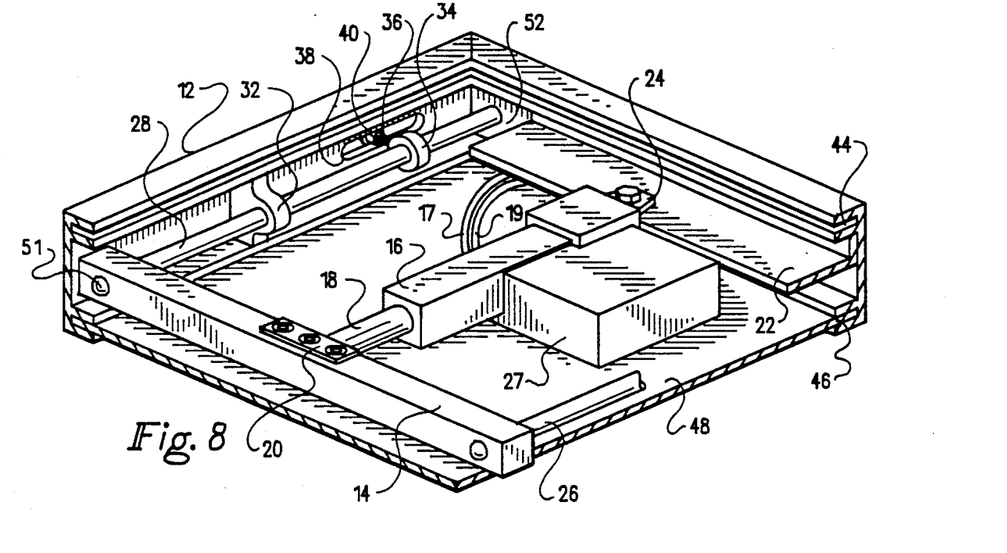
FIG. 8 is a partial bottom perspective view, with the bottom cover plate removed, illustrating the linear slide yoke and linear actuator components of the spinal positioning frame.

As best shown in FIG. 3, guide rods 26 and 28 disposed in spaced parallel relation are connected to opposite ends of the transverse yoke 14 for movement therewith. Slidable guide rods 26 and 28 are mounted by respective posterior journal bearing blocks 30 and 32 which are fixed to the frame 12. FIG. 8 illustrates an anterior journal bearing block 52 supporting the guide rod 28. An additional anterior bearing block identical to the bearing block 52 also supports the guide rod 26. Accordingly, it can be appreciated that selective actuation of the linear actuator 16 causes reciprocal linear sliding movement of the yoke 14 and attached guide rods 26 and 28 with respect to the rectangular frame 12.

Figure 6:
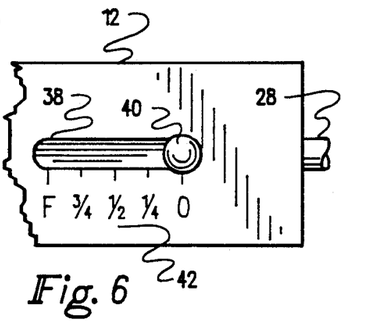
FIG. 6 is a partial right side elevational detail view illustrating the spinal frame position indicating meter.
Figure 9:
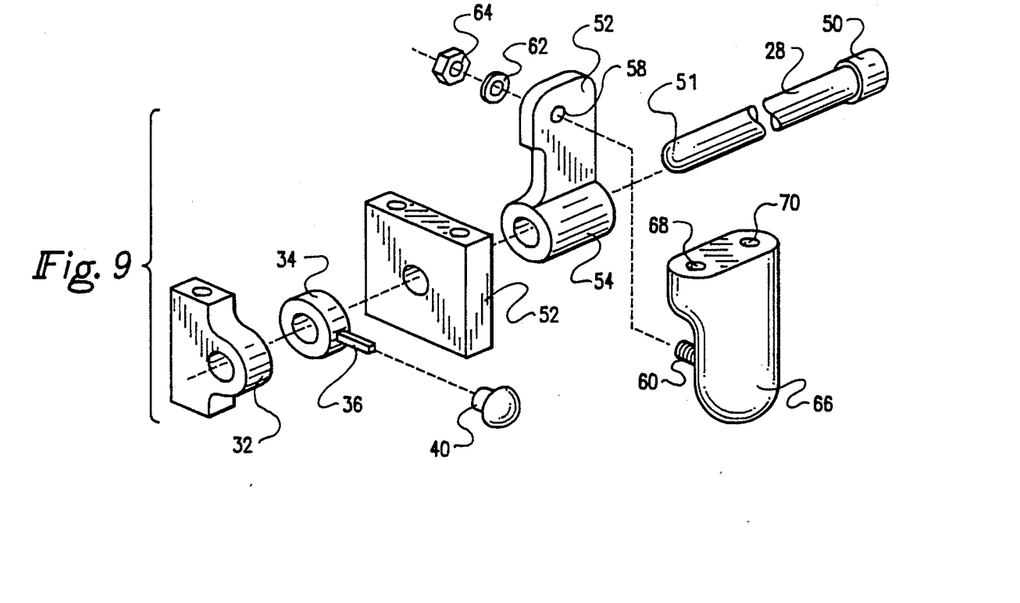
FIG. 9 is an exploded perspective detail view illustrating the linear guide rod and pivotal actuating linkage of the spinal positioning frame.
Figure 10:
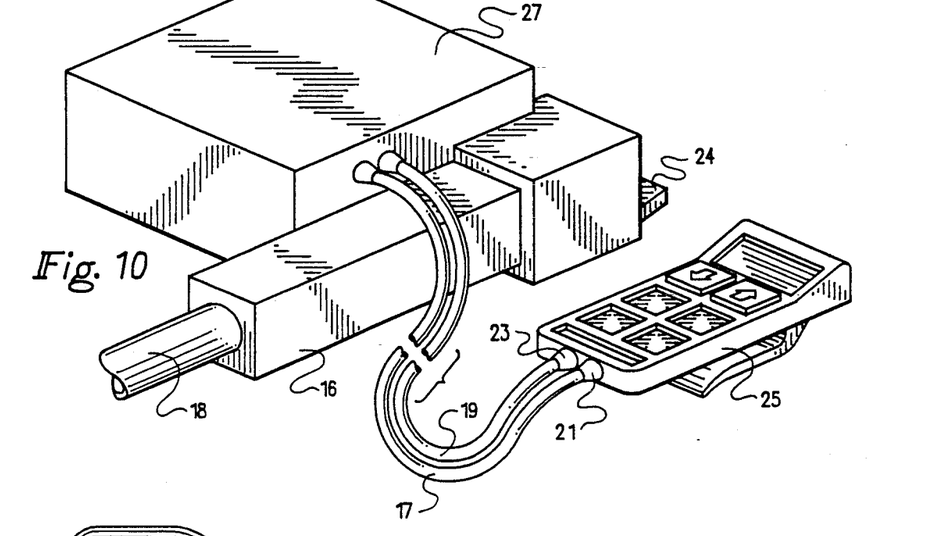
FIG. 10 is a perspective detail view illustrating the linear actuator and control components of the spinal positioning frame.

As best shown in FIGS. 8 and 9, a cylindrical collar 34 is secured for movement with the guide rod 28. Suitable fastening means, for example, a set screw, may be utilized to effect fixation of the collar 34 at a selected position along the guide rod 28. A shaft 36 extending radially from the collar 34 projects through an elongated slot 38 formed in a side wall of the rectangular frame 12. An indicator knob 40 is secured to the radial shaft 36. As can be appreciated from FIG. 6, an indicating scale including indicia 42 is provided on an external, visible portion of the rectangular frame 12, along the length of the slot 38. Accordingly, the indicator 40 indicates the relative position of the guide rod 28 with respect to the frame 12. A similar indicator and scale may be associated with guide rod 26 to allow observation from either side of the frame 12.

As shown in FIG. 8, the frame 12 is constructed by the joinder of essentially identical rectangular channel frame rail portions including spaced longitudinal grooves 44 and 46. The frame rail members forming the rectangular frame 12 are preferably formed from a lightweight rigid metal material, for example magnesium. The frame rail members may be formed in the illustrated configuration by a conventional extrusion process. The internal working mechanisms of the surgical spinal positioning frame 10 are protected from dirt and other potential contaminants by a pair of plastic cover plates, the top one of which is illustrated at 48 and disposed within groove 46. It should be understood that an essentially identical bottom cover plate will be disposed within groove 44.

As can be appreciated from FIGS. 1 and 9, a smaller diameter end of each of the guide rods 26 and 28, for example end 51 of guide rod 28, is inserted through a cylindrical-sleeve 54, through an anterior bearing block 52, and subsequently through a posterior bearing block 32. The larger diameter end 50 of the guide rod 28 is secured to the cylindrical sleeve 54. The guide rod 26 is similarly secured to a sleeve 72. A pair of pivot brackets 66 and 74 are fixedly secured to a bottom side of a rigid aluminum anterior fulcrum plate 78. As shown in FIGS. 7 and 9, securement of the pivot brackets, for example pivot bracket 66 to the fulcrum plate 78, may be effected by threaded fasteners cooperating with threaded cylindrical bores 68 and 70 formed in the pivot bracket 66. Alternative methods of securement such as epoxy, welding and rivets may be employed without departing from the scope of the present invention. Sleeves 54 and 72 include respective integrally formed radially extending tab portions 56 and 76 which are pivotally secured to brackets 66 and 74. As shown in FIG. 9, this pivotal securement may be effected by extending a threaded stud 60 secured to the particular bracket, for example bracket 66, through a slightly oversized aperture 58 in the tab portion 56 of the sleeve 54. A suitable washer 62 and nut 64 is then utilized to pivotally connect the bracket 66 with the tab 56. The anterior or front fulcrum plate 78 includes a generally semi-circular recess 80 to accommodate the throat region of a patient. The anterior fulcrum plate 78 is preferably covered by a suitable padding material removably connected by suitable fasteners such as cooperating hook and loop pile type fasteners (VELCRO ®), snaps or zippers.

As best shown in FIG. 7, a posterior rigid aluminum fulcrum plate 86 is juxtaposed with the anterior fulcrum plate 78, and is also preferably covered by suitable removable padding. The fulcrum plates 78 and 86 include aligned longitudinally extending leg portions 82, 84, 88 and 90. As can be appreciated from FIGS. 1 and 7, elongated relatively narrow flex strips 92 and 94 extend along and connect the leg portions 84, 90, and 82, 88 of the fulcrum plates 78 and 86. The flex strips 92 and 94 extend in spaced parallel relation and are preferably formed from a flexible clock steel material. The flex strips 92 and 94 are secured to the fulcrum plates 78 and 86 by conventional fastening means such as screws, rivets, welding or epoxy. A preferred securement method employs a combination of rivets and epoxy.

A pair of pivotal mounting tabs 96 and 98 are secured to the underside of the anterior fulcrum plate 86 by suitable fasteners. Cooperating pivot tabs 100 and 102 are formed at posterior corner regions of the rectangular frame 12. Suitable fasteners such as pivot bolts, screws or pins pivotally mount the tabs 96 and 98 to the tabs 100 and 102.

Figures 11, 12:
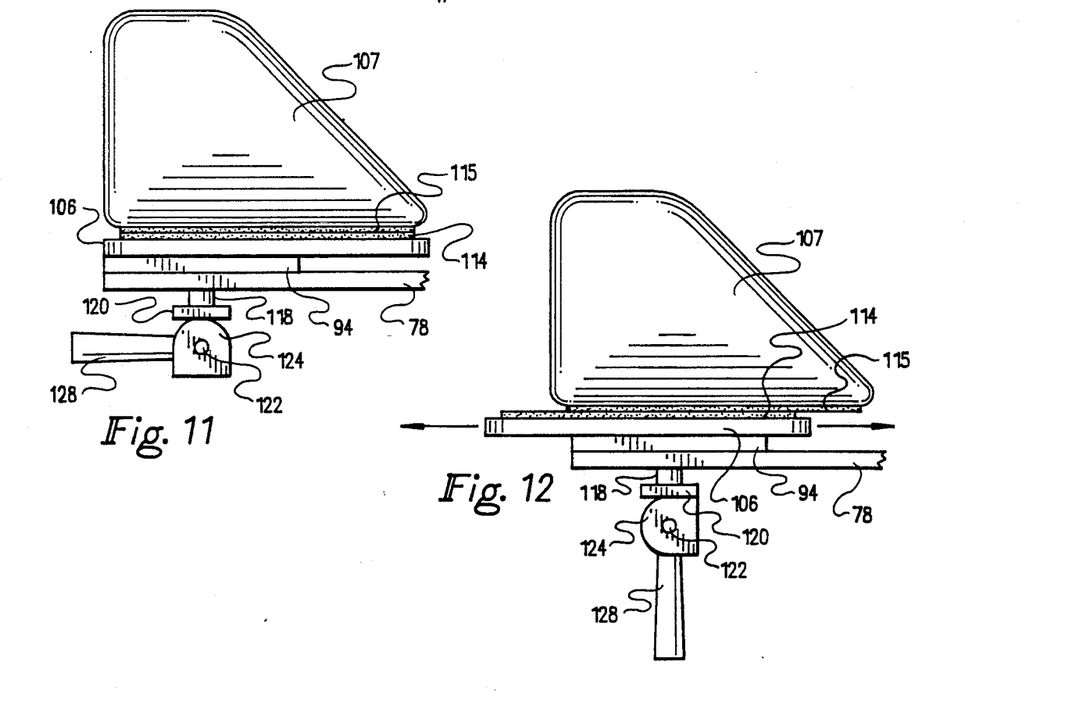
FIG. 11 is a front end elevational detail view illustrating the support pad adjusting mechanism of the spinal positioning frame clamped in a selected adjusted position.
FIG. 12 is a front end elevational view illustrating the support pad adjusting mechanism of the spinal positioning frame unclamped to allow selective adjustment.

With reference to FIGS. 1 and 7, a pair of pyramidal patient support pads 105 and 107 are adjustably secured by cooperating hook and loop pile type fasteners, preferably the type sold under the trademark VELCRO ®, to respective pad mounting plates 104 and 106. Specifically, pad 105 is secured to fastener 112 extending substantially along the upper surface of the mounting plate 104, while pad 107 is similarly secured to fastener 114 extending substantially along the length of mounting plate 106. The pad mounting plates 104 and 106 are in turn secured, respectively, to flex strips 92 and 94. In order to enable lateral adjustment of the pad mounting plates 104 and 106 with respect to the flex strips 92 and 94, laterally elongated slots 108 and 110 are provided at opposite ends of each of the pad mounting plates 104 and 106. Quick release cam lock fasteners cooperate with bolts 116 to rapidly lock and release the pad mounting plates 104 and 106 in selected laterally adjusted positions. With reference to FIGS. 7 and 11, each of the cam lock fasteners includes a screw 116 with an enlarged head which is first inserted through the slot, for example slot 110 in pad mounting plate 106. The screw 116 also extends through a slightly oversized circular aperture formed in the associated flex strip 94 and subsequently through a similar aperture in the fulcrum plate 78. An internally threaded cylindrical barrel 118 is slidably received through a central aperture in a rectangular tab 120. Integrally formed cam lobe members 124, 126 and handle 128 are pivotally secured to a lower end portion of the barrel 118 by a pin 122. In the clamped position shown in FIG. 11, the cam lobes 124 and 126 abut the tab 120 which is mounted for axial sliding movement on the threaded cylindrical barrel 118. As the tab 120 is moved into abutment with the bottom surface of the fulcrum plate 178, the barrel 118 and screw 116 will be pulled downwardly, clamping the mounting plate 106 in a selected laterally adjusted position onto the flex strip 94. When lateral adjustment of the patient mounting pad 107 is required, it may be achieved by moving the handle 128 of the cam lock fastener to the unclamped position shown in FIG. 12 and subsequently sliding the mounting plate 106 to the desired laterally adjusted position. As an alternative mechanism for effecting additional lateral adjustment, the pile fastener 115 fixedly mounted to the bottom surface of the pad 107 may be reoriented with respect to the cooperating pile fastener 114 fixedly secured to the upper face of the mounting plate 106.

Figure 2:
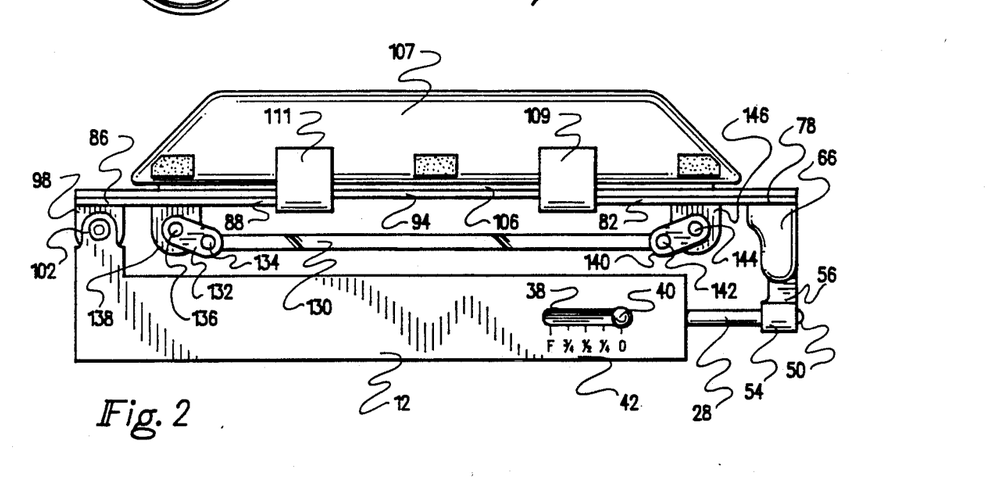
FIG. 2 is a right side elevational view of the surgical spinal positioning frame in a fully lowered position.

With reference to FIGS. 1, 2 and 7, a rectangular transparent bridge 130 is preferably formed from a plastic material, such as the type sold under the trademark LEXAN. A plurality of pivotal links 132, 140, 152 and 154 are secured to corner portions of the bridge 130, at opposite ends of cylindrical shaft portions 148 and 150. Opposite ends of the pivotal links 132, 140, 152 and 154 are pivotally secured to fixed tabs projecting downwardly in aligned pairs from fulcrum plates 78 and 86. For example, with reference to FIG. 2, link 132 is pivotally secured to bridge 130 by screw 134 and to pivot bracket 138 by screw 136. Similarly, link 140 is pivotally secured to bridge 130 by screw 142 and to fixed pivot bracket 146 by screw 144. As shown in FIG. 7, link 154 is secured to a fixed pivot bracket 156 disposed on the underside of anterior fulcrum plate 78.

Figure 13:
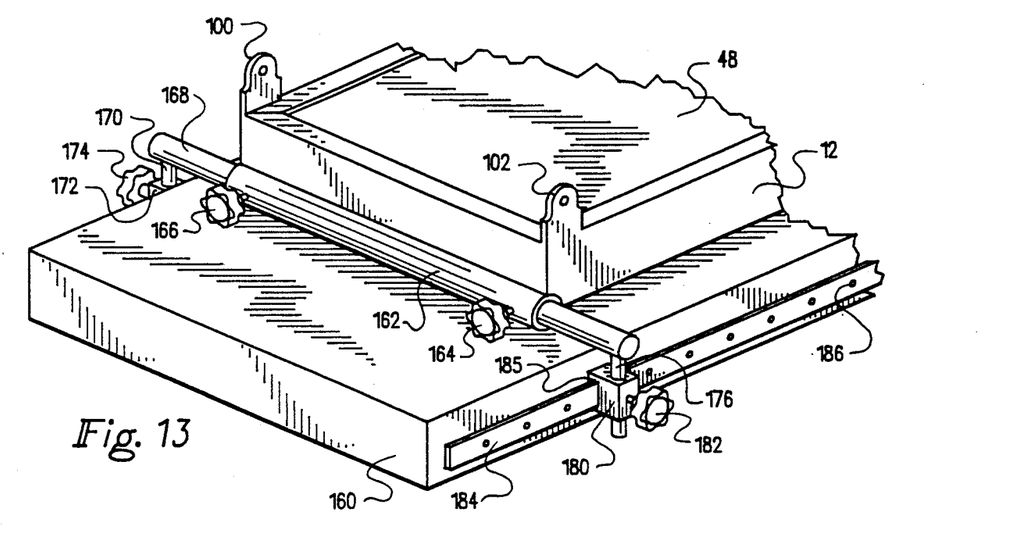
FIG. 13 is a partial perspective view illustrating the spinal positioning frame mounted for selective independent lateral and longitudinal adjustment on an operating table.
Figures 14, 15:
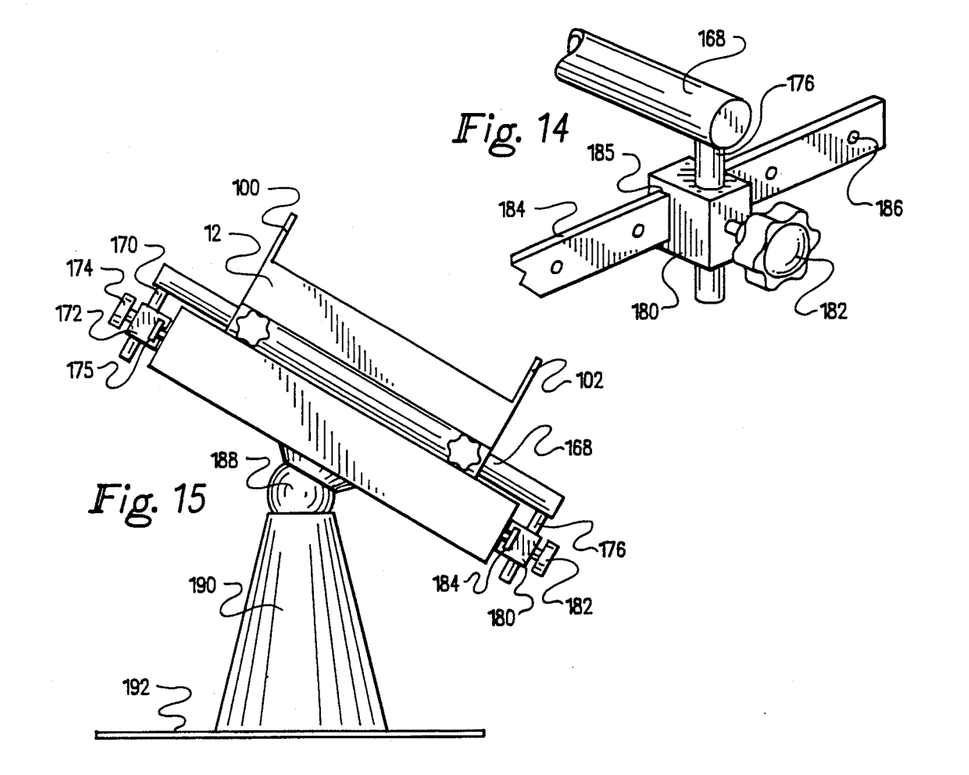
FIG. 14 is a perspective detail view further illustrating the longitudinal adjustment mechanism of FIG. 13.
FIG. 15 is a rear (posterior) end elevational view illustrating the spinal positioning frame mounted for independent lateral, longitudinal and pivotal adjustment on an operating table.

With reference now to FIGS. 13 through 15, a preferred mounting of the surgical spinal positioning frame 10 on an operating table will now be described. The rectangular frame 12 is preferably provided at each opposite end with a fixed cylindrical tube 162 mounted for sliding movement on a lateral positioning rod 168. The frame 12 is secured in a selected laterally adjusted position by tightening set screws 164 and 166 which extend through threaded apertures provided in sleeve 162 and into frictional abutment with rod 168. Shafts 170 and 176 are fixed at opposite ends of rod 168 and project radially downwardly into respective slide blocks 172 and 180. Set screws 174 and 182 extend in threaded engagement through slide blocks 172, 180, shafts 170 and 176, and into abutment with a respective linear longitudinal guide rails 175 and 184. Longitudinally extending linear guide rails 175 and 184 are preferably provided with a plurality of spaced detent apertures 186, to allow a wide range of longitudinal adjustment in discrete, predetermined increments. As shown in FIG. 14, slide block 180 is provided with a slot 185 through which linear guide rail 184 is received. As shown in FIG. 15, the operating table 160 is preferably mounted by a ball and socket pivot mechanism 188 on an upstanding vertical support member 190 secured to a horizontal base 192. In this manner, the frame 12 is mounted for independent lateral, longitudinal and pivotal adjustment to afford maximum flexibility in patient orientation for any given surgical procedure.

Figure 4:
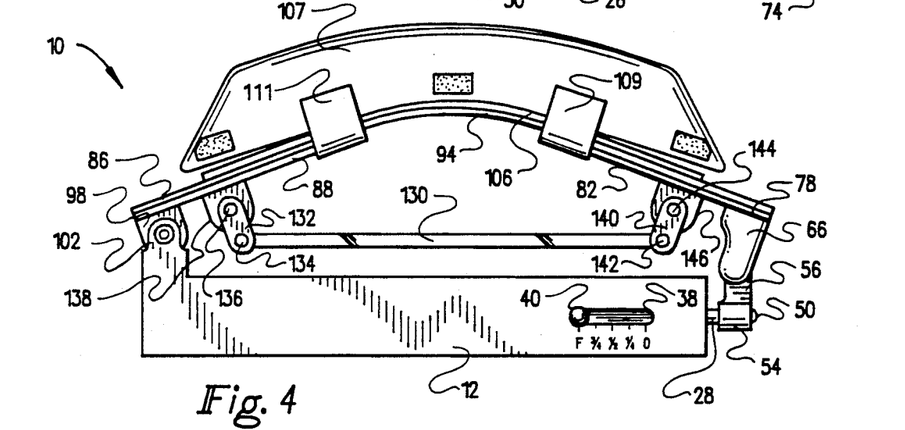
FIG. 4 is a is a right side elevational view of the surgical spinal positioning frame in a fully elevated position.

With reference to FIGS. 1, 2 and 4, the surgical spinal positioning frame 10 is initially provided with suitable removable padded coverings over fulcrum plates 78 and 86. A patient lies face downwardly, with their throat region disposed in recess 80 in the anterior fulcrum plate 78. The pads 105 and 107 are adjusted to accommodate the particular patient's physique, and are secured in the adjusted position by the mechanism illustrated in FIGS. 11 and 12. Additionally, straps 109 and 111 may also be provided to enhance securement of the pads in a selected adjusted position. Straps 109 and 111 are preferably secured by cooperating hook and loop pile type fasteners. After the patient has been properly situated between pads 105 and 107, suitable seat belt type straps (not shown) may be utilized to secure the patient in position between the pads 105 and 107 on the frame 12. Accordingly, the frame 12 and patient supported thereon are then adjusted to a desired lateral, longitudinal and pivotal adjusted position on the operating table 160, as shown in FIG. 15. When the desired adjusted position has been achieved, the remote control unit 25 may be actuated to cause the pads 105 and 107 to bow convexly to the desired extent. FIG. 2 illustrates the spinal position frame 10 in a fully lowered position, with the indicator 40 disposed at the zero position of the scale 42. As the linear actuator causes the yoke 14 (FIG. 3) to move toward the anterior end of the frame 12, the flex strips 92 and 94 are forced to flex upwardly into the convex curvature illustrated in FIG. 4. In the fully elevated position shown, the indicator 40 has moved to the left hand position on the scale 42. Due to the pivotal parallelogram linkage mounting of the bridge 130, the bridge 130 remains in a horizontal orientation, parallel with the horizontal plane of the rectangular frame 12. Because the bridge 130 is formed from a plastic material, such as the type sold under the trademark LEXAN, it is transparent to X-rays. Accordingly, a conventional X-ray cassette may be inserted into the space between the bridge 130 and the top cover plate 48. A conventional X-ray machine may then be utilized to locate surgical coordinates prior to surgery, and also to subsequently check and document results of a surgical procedure, without removing the patient from the positioning frame 10. In the elevated positions shown in FIG. 4, the bridge 130 is disposed for providing sufficient support to a patient's abdomen, while still allowing sufficient clearance to avoid excessive abdominal pressure.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A surgical spinal positioning device, comprising:
   a frame;
   a pair of spaced elongated members on said frame defining a region for supporting at least a portion of a patient's torso therebetween;
   means for selectively bending said elongated members to regulate spinal curvature of a patient;
   a substantially central region between said elongated members unobstructed by non-X-ray transmissive materials; and
   a bridge formed from an X-ray transparent material suspended beneath and between said elongated members for supporting a patient's abdomen, said bridge defining a space between said bridge and said frame dimensioned for insertion of an X-ray cassette whereby X-rays may be taken of a patient supported on said surgical spinal positioning device to facilitate preoperative determination of surgical coordinates and postoperative checking and documentation of surgical results.

2. The surgical spinal positioning device of claim 1, further comprising a meter for indicating an extent of bending of said elongated members.

3. The surgical spinal positioning device of claim 1, wherein said elongated members comprise pads secured to elongated flex strips.

4. The surgical spinal positioning device of claim 1, further comprising a pivotal linkage assembly suspending said bridge beneath said elongated members such that said bridge is substantially maintained in a horizontal orientation irrespective of the degree of bending of said elongated members.

5. The surgical spinal positioning device of claim 1, further comprising means for adjusting said elongated members with respect to said frame.

6. The surgical spinal positioning device of claim 5, wherein said means for adjusting said elongated members comprises cooperating hook and loop pile fasteners.

7. The surgical spinal positioning device of claim 5, wherein said means for adjusting said elongated members comprises quick release cam lock fasteners.

8. A surgical spinal positioning device, comprising:
   a frame;
   a pair of spaced elongated members on said frame defining a region for supporting at least a portion of a patient's torso therebetween;
   a pair of elongated flex strips secured to said elongated members;
   a fulcrum plate pivotally mounted on said frame and secured to first ends of said flex strips;
   a linear actuator; and
   means securing second ends of each of said flex strips to said linear actuator such that linear movement of said actuator effects bending of said flex strips for selectively bending said elongated members to regulate spinal curvature of a patient.

9. The surgical spinal positioning device of claim 8, wherein said means securing second ends of said flex strips to said linear actuator comprises a fulcrum plate secured to said second ends of said flex strips and pivotally secured to said linear actuator.

10. The surgical spinal positioning device of claim 8, wherein said means securing second ends of said flex strips to said linear actuator comprises:
    a yoke connected to said linear actuator and mounted for reciprocal sliding movement in said frame;
    a pair of guide rods secured for movement with said yoke; and means securing said second ends of said flex strips to said guide rods.

11. The surgical spinal positioning device of claim 10, wherein said means securing said second ends of said flex strips to said guide rods comprises a fulcrum plate secured to said second ends of said flex strips and pivotally secured to said guide rods.

12. The surgical spinal positioning device of claim 8, further comprising a bridge secured beneath and between said elongated members for supporting a patient's abdomen.

13. The surgical spinal positioning device of claim 12, further comprising a pivotal linkage assembly suspending said bridge beneath said elongated members such that said bridge is substantially maintained in a horizontal orientation irrespective of the degree of bending of said elongated members.

14. The surgical spinal positioning device of claim 8, further comprising a meter for indicating an extent of bending of said elongated members.

15. The surgical spinal positioning device of claim 8, further comprising means for adjusting said elongated members with respect to said frame including cooperating hook and loop pile fasteners.

16. The surgical spinal positioning device of claim 8, further comprising means for adjusting said elongated members with respect to said frame including quick release cam lock fasteners.

17. A surgical spinal positioning device, comprising:
a frame;
a pair of spaced elongated members on said frame defining a region for supporting at least a portion of a patient's torso therebetween;
a pair of elongated flex strips secured to said elongated members;
a first fulcrum plate pivotally mounted on said frame and secured to first ends of said flex strips;
a linear actuator;
a yoke connected to said linear actuator and mounted for reciprocal sliding movement in said frame;
a pair of guide rods secured for movement with said yoke; and
a second fulcrum plate secured to second ends of said flex strips and pivotally secured to said guide rods such that linear movement of said actuator effects bending of said flex strips for selectively bending said elongated members to regulate spinal curvature of a patient.

18. The surgical spinal positioning device of claim 17, further comprising a bridge secured beneath and between said elongated members for supporting a patient's abdomen.

19. The surgical spinal positioning device of claim 18, further comprising a pivotal linkage assembly suspending said bridge beneath said elongated members such that said bridge is substantially maintained in a horizontal orientation irrespective of the degree of bending of said elongated members.

20. The surgical spinal positioning device of claim 17, further comprising a meter for indicating an extent of bending of said elongated members.

* * * * *